United States Patent
Kahn et al.

(10) Patent No.: US 7,747,735 B1
(45) Date of Patent: Jun. 29, 2010

(54) METHOD AND APPARATUS FOR SEAMLESSLY ACQUIRING DATA FROM VARIOUS SENSOR, MONITOR, DEVICE (SMDS)

(75) Inventors: Philippe Kahn, Aptos, CA (US); Arthur Kinsolving, Santa Cruz, CA (US)

(73) Assignee: DP Technologies, Inc., Scotts Valley, CA (US)

( * ) Notice: Subject to any disclaimer, the term of this patent is extended or adjusted under 35 U.S.C. 154(b) by 627 days.

(21) Appl. No.: 11/346,720

(22) Filed: Feb. 2, 2006

(51) Int. Cl.
*A61N 5/00* (2006.01)
*G06F 15/173* (2006.01)

(52) U.S. Cl. ............................ 709/224; 600/301
(58) Field of Classification Search ......... 709/203–207, 709/223–226, 202, 201, 200; 715/222–226; 600/300, 301, 306–307
See application file for complete search history.

(56) References Cited

U.S. PATENT DOCUMENTS

| | | | |
|---|---|---|---|
| 5,737,439 A * | 4/1998 | Lapsley et al. ............... 382/115 |
| 5,771,001 A | 6/1998 | Cobb | |
| 6,595,929 B2 | 7/2003 | Stivoric et al. | |
| 7,379,999 B1 | 5/2008 | Zhou et al. | |
| 7,457,872 B2 | 11/2008 | Aton et al. | |
| 2002/0138017 A1 | 9/2002 | Bui et al. | |
| 2003/0101260 A1 | 5/2003 | Dacier et al. | |
| 2003/0139908 A1 | 7/2003 | Wegerich et al. | |
| 2003/0149526 A1 | 8/2003 | Zhou et al. | |
| 2003/0208113 A1 | 11/2003 | Mault et al. | |
| 2003/0227487 A1* | 12/2003 | Hugh ........................... 345/777 |
| 2003/0236625 A1 | 12/2003 | Brown et al. | |
| 2004/0017300 A1 | 1/2004 | Kotzin et al. | |
| 2004/0024846 A1 | 2/2004 | Randall et al. | |
| 2004/0043760 A1 | 3/2004 | Rosenfeld et al. | |
| 2004/0044493 A1 | 3/2004 | Coulthard | |
| 2004/0078219 A1 | 4/2004 | Kaylor et al. | |
| 2004/0078220 A1 | 4/2004 | Jackson | |
| 2004/0122294 A1 | 6/2004 | Hatlestad et al. | |
| 2004/0122295 A1 | 6/2004 | Hatlestad et al. | |
| 2004/0122296 A1 | 6/2004 | Hatlestad et al. | |

(Continued)

FOREIGN PATENT DOCUMENTS

WO    WO 02/088926 A1    11/2002

OTHER PUBLICATIONS

PCT Notification Preliminary Report on Patentability, PCT/US2006/29570, mailing date: Feb. 7, 2008, 6 pages.

(Continued)

*Primary Examiner*—Asad M Nawaz
(74) *Attorney, Agent, or Firm*—Blakely, Sokoloff, Taylor & Zafman, LLP; Judith A. Szepesi

(57) ABSTRACT

A method and apparatus to provide user data through a monitor, alert, control, and share (MACS) device comprising a data receiving logic to receive intermittent data from a user about readings from a real sensor, monitor or device (SMD), from a user and a verification engine to verify that the data is accurate prior to adding it to a database. The apparatus further comprising an intelligent notification engine to communicate with the user and a presentation layer to enable a user to interface with the always-on virtual MACS device, the always-on virtual MACS device providing data regardless of a status of the real SMD.

20 Claims, 9 Drawing Sheets

U.S. PATENT DOCUMENTS

| | | |
|---|---|---|
| 2004/0122297 A1 | 6/2004 | Stahmann et al. |
| 2004/0122333 A1 | 6/2004 | Nissila |
| 2004/0122484 A1 | 6/2004 | Hatlestad et al. |
| 2004/0122485 A1 | 6/2004 | Stahmann et al. |
| 2004/0122486 A1 | 6/2004 | Stahmann et al. |
| 2004/0122487 A1* | 6/2004 | Hatlestad et al. ............... 607/60 |
| 2004/0146048 A1 | 7/2004 | Cotte |
| 2004/0148340 A1 | 7/2004 | Cotte |
| 2004/0148341 A1 | 7/2004 | Cotte |
| 2004/0148342 A1 | 7/2004 | Cotte |
| 2004/0148351 A1 | 7/2004 | Cotte |
| 2004/0148392 A1 | 7/2004 | Cotte |
| 2004/0259494 A1 | 12/2004 | Mazar |
| 2005/0038691 A1 | 2/2005 | Babu |
| 2005/0079873 A1 | 4/2005 | Caspi et al. |
| 2005/0101841 A9 | 5/2005 | Kaylor et al. |
| 2005/0102167 A1 | 5/2005 | Kapoor |
| 2005/0107944 A1 | 5/2005 | Hovestadt et al. |
| 2005/0113650 A1* | 5/2005 | Pacione et al. ............... 600/300 |
| 2005/0131736 A1 | 6/2005 | Nelson et al. |
| 2005/0182824 A1 | 8/2005 | Cotte |
| 2005/0235058 A1 | 10/2005 | Rackus et al. |
| 2005/0262237 A1 | 11/2005 | Fulton et al. |
| 2006/0109113 A1 | 5/2006 | Reyes et al. |
| 2006/0154642 A1 | 7/2006 | Scannell, Jr. |
| 2006/0161459 A9 | 7/2006 | Rosenfeld et al. |
| 2007/0024441 A1* | 2/2007 | Kahn et al. ............ 340/539.22 |
| 2007/0050157 A1 | 3/2007 | Kahn et al. |
| 2007/0192483 A1 | 8/2007 | Rezvani et al. |
| 2009/0099668 A1 | 4/2009 | Lehman et al. |

OTHER PUBLICATIONS

PCT International Search Report and the Written Opinion of the International Searching Authority, PCT/US2006/29570, mailing date Jul. 17, 2007, 7 pages.

* cited by examiner

[ Date Control 705 ]
[ Time Zone 710 ]

① Date of tests

I am entering results for  ☑ today  OR  ☐ [Dec ▾] [10 ▾] [2005 ▾]

Select the time zone in which these tests were taken:

[San Francisco (GMT -8 PST) ▾]   current time in this zone is: 8:10 pm

[ Test Types 715 ]

② Test Types

I would like to enter my:  ☑ select all

☐ blood pressure & heart rate   ☐ body weight & fat   ☐ pedometer
☐ blood glucose

[ Variable A Input 720 ]

③ Enter Values   ☐ enter current time for all values

A. systolic BP / diastolic BP: [    ] / [    ] mmHg heart rate: [    ] BPM

[ Variable B Input 725 ]

time of test: ☐ now  OR  ☐ [12 ▾] [00 ▾] [AM ▾]

730

B. body weight: [    ] [LBS ▾]   body fat: [    ] % time of test: ☐ now  OR  ☐ [12 ▾] [00 ▾] [AM ▾]

735

C. pedometer: [    ] steps time of test: ☐ now  OR  ☐ [12 ▾] [00 ▾] [AM ▾]

740

D. blood glucose: [    ] mg/dL   test type: [ ▾]

time of test: ☐ now  OR  ☐ [12 ▾] [00 ▾] [AM ▾]

745

☐ send me a health report   [ upload values ]

Figure 7

METHOD AND APPARATUS FOR SEAMLESSLY ACQUIRING DATA FROM VARIOUS SENSOR, MONITOR, DEVICE (SMDS)

FIELD OF THE INVENTION

The present invention relates to a method and apparatus to enable data acquisition from various devices.

BACKGROUND

There are many sensors, monitors, and devices (SMDs) that are not "connected." Connected, in this context, means that the SMD is capable of sending its data, in addition to, or instead of, displaying it to the user. These unconnected devices output data to a user, but do not connect to external systems.

Great strides could be made in living with and treating chronic conditions such as hypertension, heart disease and diabetes, if user data could be entered to a central database for analysis on a regular basis with little hassle.

BRIEF DESCRIPTION OF THE DRAWINGS

The present invention is illustrated by way of example, and not by way of limitation, in the figures of the accompanying drawings and in which like reference numerals refer to similar elements and in which:

FIG. 7 illustrates an exemplary web input interface which may be used.

DETAILED DESCRIPTION

The method and apparatus described is the ability to obtain SMD information from non-connected SMDs using a simple interface, such as electronic mail (e-mail), short message system (SMS), multimedia messaging system (MMS), instant messaging system (IM), or other such interfaces. These interfaces have the advantage that they do not require the user to navigate to a particular web site. Rather, the user's existing interface with the electric world is utilized to obtain data. E-mail is particularly useful for obtaining data from less technologically savvy clients. E-mail is becoming a standard of everyone's life. Everyone from teenagers to grandmothers check e-mail on a regular basis, whether from home or from their workplace, e-mail kiosks, or internet cafes. E-mail is the most widely understood interface on the Internet. There are many users who have a basic understanding of the e-mail interface; e-mail is becoming a standard of everyone's life.

Many users who have basic understanding of the e-mail interface have trouble navigating to a web page and understanding the flow of a web page. Almost everyone now, grandmothers and children included, can send and receive e-mail. This is completely understandable as every web page has its own interface with its own navigation system whereas e-mail has one consistent interface that never changes. Therefore, in one embodiment, the system takes advantage of this consistent and well-understood paradigm and uses an email-based interface to request and receive SMD data.

Figure 1A:
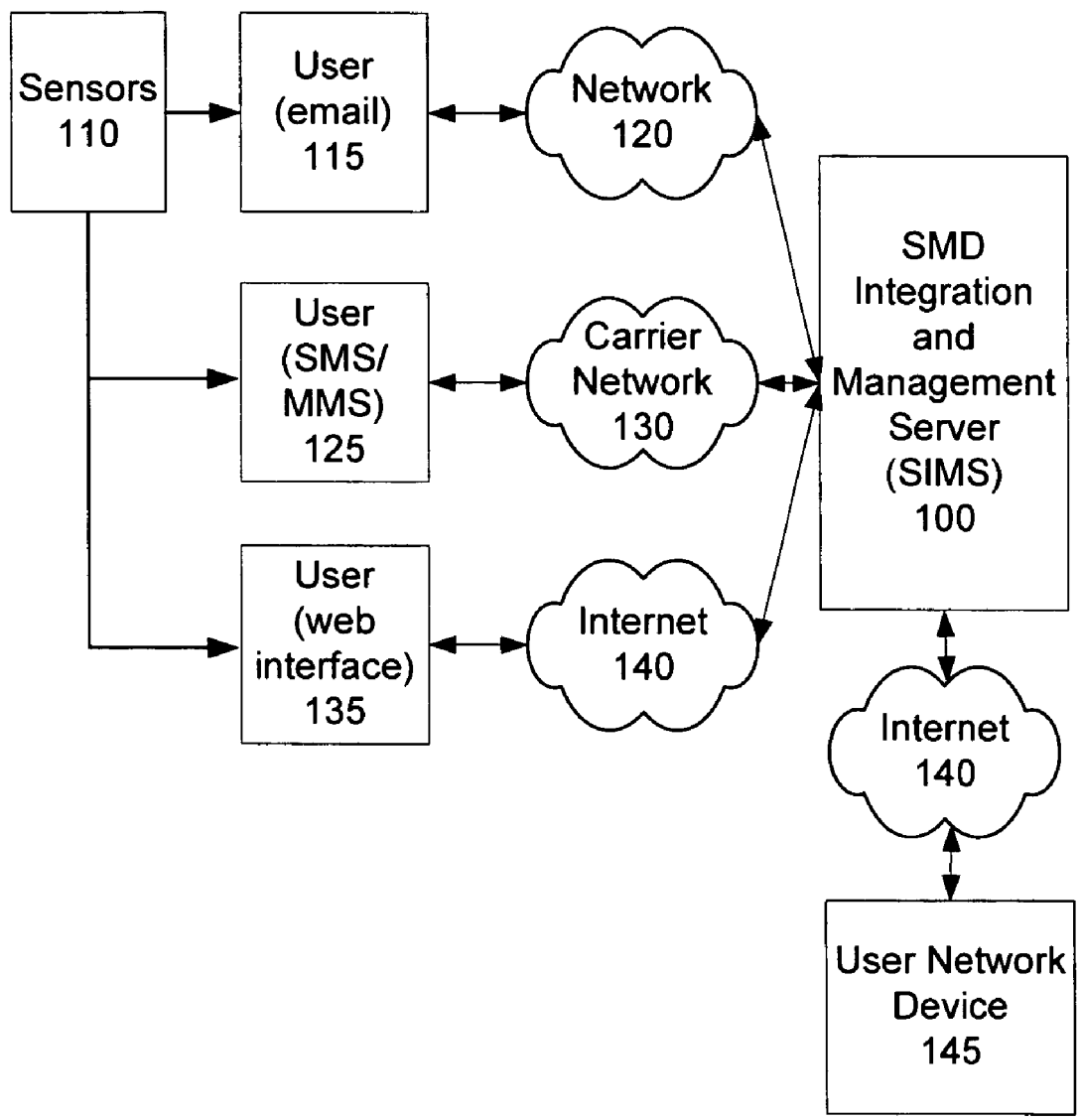
FIG. 1A is a block diagram of one embodiment of the interconnections between the various elements of the system.

FIG. 1A is a network diagram of one embodiment of the various elements of the system. The various SMDs 110 are available to users. Users can send data through various means to the SMD Integration and Management Server (SIMS) 100. Users may send data through SMS or MMS 125, coupled through carrier network 130, or using a web interface or instant messaging system 135 coupled through the Internet 140, or they may be coupled through an e-mail interface 115 through network 120 to SIMS 150.

SIMS 100 includes or communicates with a MACS device (not shown). The MACS device is then accessible via the Internet 140, carrier network 130, or some other means to various user devices 145.

Figure 1B:
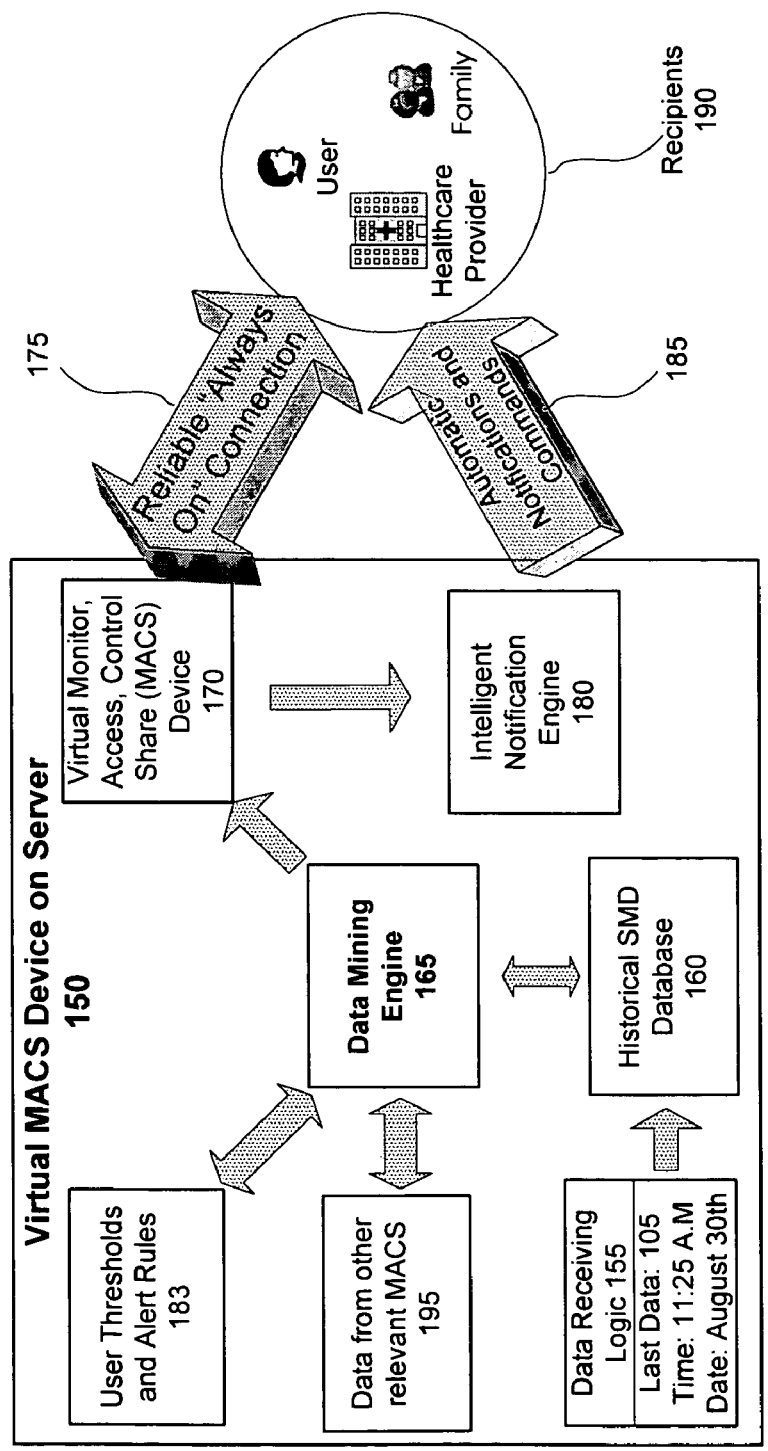
FIG. 1B is a system diagram illustrating one embodiment of the central server and its connections.

FIG. 1B is a block diagram illustrating one embodiment of the MACS device and its relationship to the actual SMD. The actual SMD 110 has an intermittent connection to a server which includes the virtual MACS Device 150. The connection 115 may be through the Internet, through a carrier network, or through other means. The server 120 may be located in the same location as the real SMD 110.

The data receiving logic 155 receives the data from the user via an intermittent connection. The data is stored in historical database 160. The historical data is used by data mining engine 165, to present virtual MACS device 170 via a reliable always-on connection 175 to various recipients 190. In a healthcare setting for example, the recipients may include the user, healthcare providers, and family. For environmental monitors, the recipients may include the responsible local and state officials, local residents, or other relevant recipients.

In one embodiment, data mining engine 165 may further interface with user alerts and rules 183 to generate notifications through intelligent notification engine 180. Intelligent notification engine 180 can send automatic notifications to designated recipients 190, when certain threshold or alert conditions are met. The threshold or alert conditions may include historical data, trend analysis, variance from charted trends, simple threshold, or any combination of the use of historical and current data from the actual SMD 110. In one embodiment, the data mining engine 165 constantly monitors the database 160, to ensure that the alert rules and user thresholds 183 have not been triggered. Intelligent notification engine 180 can, in one embodiment, trigger a notification in an appropriate format to any designated recipient.

In one embodiment, in addition to the database 160, data from other relevant actual SMDs may be received as well via logic 195. For example, in an environmental situation, in addition to the wind speed, the barometric pressure, or other relevant conditions may be monitored. The threshold and alert rules 183 may utilize a combination of data from more than one real SMD to trigger a notification or command 180.

The Internet Interactive System of the present invention is, in one embodiment, powered by secure encrypted e-mail. While email is well understood, there are some difficulties in using e-mail for communicating information. E-mail messages can have several different formats (plain text, rich text, html, etc.) and various encodings (MIME, uuencode, etc.). Sometimes when checking on a particular device or through a particular version of web mail, e-mail messages appear completely garbled. Yet, in almost every case, the subject line readable because it is always sent in the same simple text format. Therefore, for relatively small data batch uploads, the subject bar makes sense as the conduit for data. The subject line has other advantages. It is easy to parse, since there are no line breaks, and it is size limited. Therefore, in one embodiment, the subject line of e-mail messages is used to transmit data from the user to the device, and vice versa. In another embodiment, the body of e-mail messages is used. Alternative paths, which may include instant messenger (IM), web interface, short message system (SMS), multimedia message system (SMS), and other paths, may be used.

Figure 2:
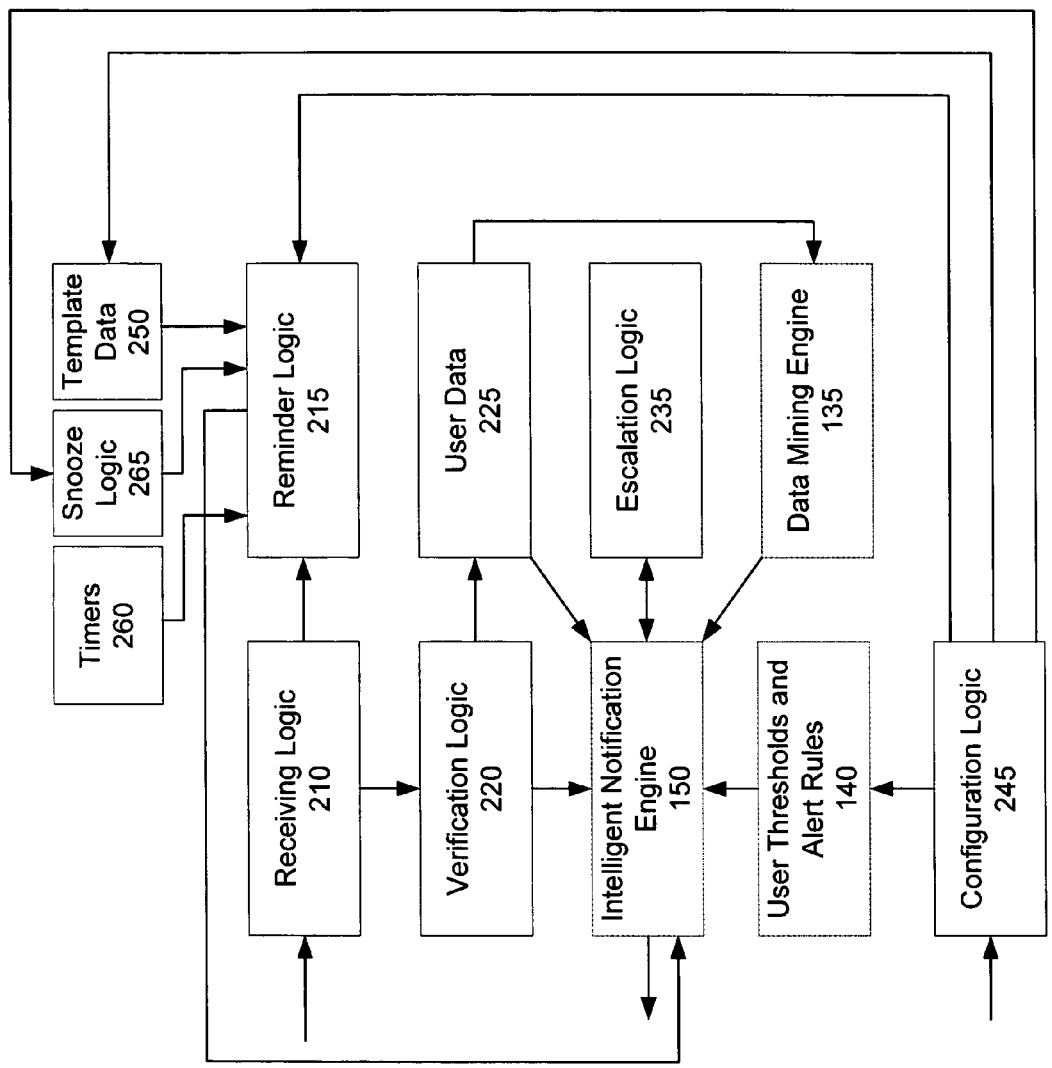
FIG. 2 is a block diagram of one embodiment of the central server.

FIG. 2 is a block diagram of one embodiment of the data receiving logic. The receiving logic 210 receives data from the user. Note that the user may be a caretaker, patient, doctor, or any other person, agency, or entity which obtains data from an SMD and sends it to the SMD Integration and Management Server (SIMS).

Reminder logic 215 monitors the data that is received, and ensures that if data is not received within the expected timeframe, a reminder message is sent out. In one embodiment, timers 260 are used to ensure that a timely reminder is sent. In one embodiment, the user may respond to a reminder with a "snooze" signal, indicating that the response will be delayed. Snooze logic 265 ensures that the reminder logic 215 doesn't escalate the failure to respond, if the snooze option is used. In one embodiment, the number of times the snooze can be used may be limited. In one embodiment, there may be an alert sent whenever the snooze option is used. For example, for a child monitoring a vital signal, the parent may be alerted when the snooze is used. In one embodiment, the availability of the snooze option and its use and limitations, is set up during configuration.

In one embodiment, reminder logic 215 sends out a prereminder, prior to the data being expected. The pre-reminder, in one embodiment, is a template, formatted for the user's interface (i.e. instant messenger, SMS, web mail, OUTLOOK™ email, etc.), with only the data missing. Templates 250 are available.

The reminder logic 215 uses the intelligent notification engine 150 to send the reminders. The intelligent notification engine 150 uses data from user thresholds and alert rules 140. The user thresholds and alert rules 140 specifies the communications paths to use for reminders.

Escalation logic 235 escalates reminders, if no response is received to a reminder. Escalation may include sending data through other paths, sending data to other persons, etc. In one embodiment, these settings may be controlled by the user through configuration logic 245.

In one embodiment, the user can, through configuration logic 245, indicate that the user will not be available to enter data. This temporarily turns off the reminder logic 215.

If data is properly received, verification logic 220 verifies it. Verification ensures that the data is likely to be accurate data, and that the data does not trigger an alert. If an alert is triggered, in one embodiment intelligent notification engine 150 sends out an alert, in accordance with the settings. In one embodiment, verification logic 220 triggers a "verification and re-measurement request" prior to sending out the alert. Depending on the severity of the alert, and the user's response, escalation logic 235 may escalate the response, as specified by user thresholds and alert rules 140.

Once data is verified, it is added to the user data 225. Data mining engine 135 analyzes the user data, to identify trends. For example, continuously increasing cholesterol levels are a risk factor, even if the absolute value is still below the "risk" level. The data mining engine 135 may also trigger an alert, based on the data analysis.

Figure 3:
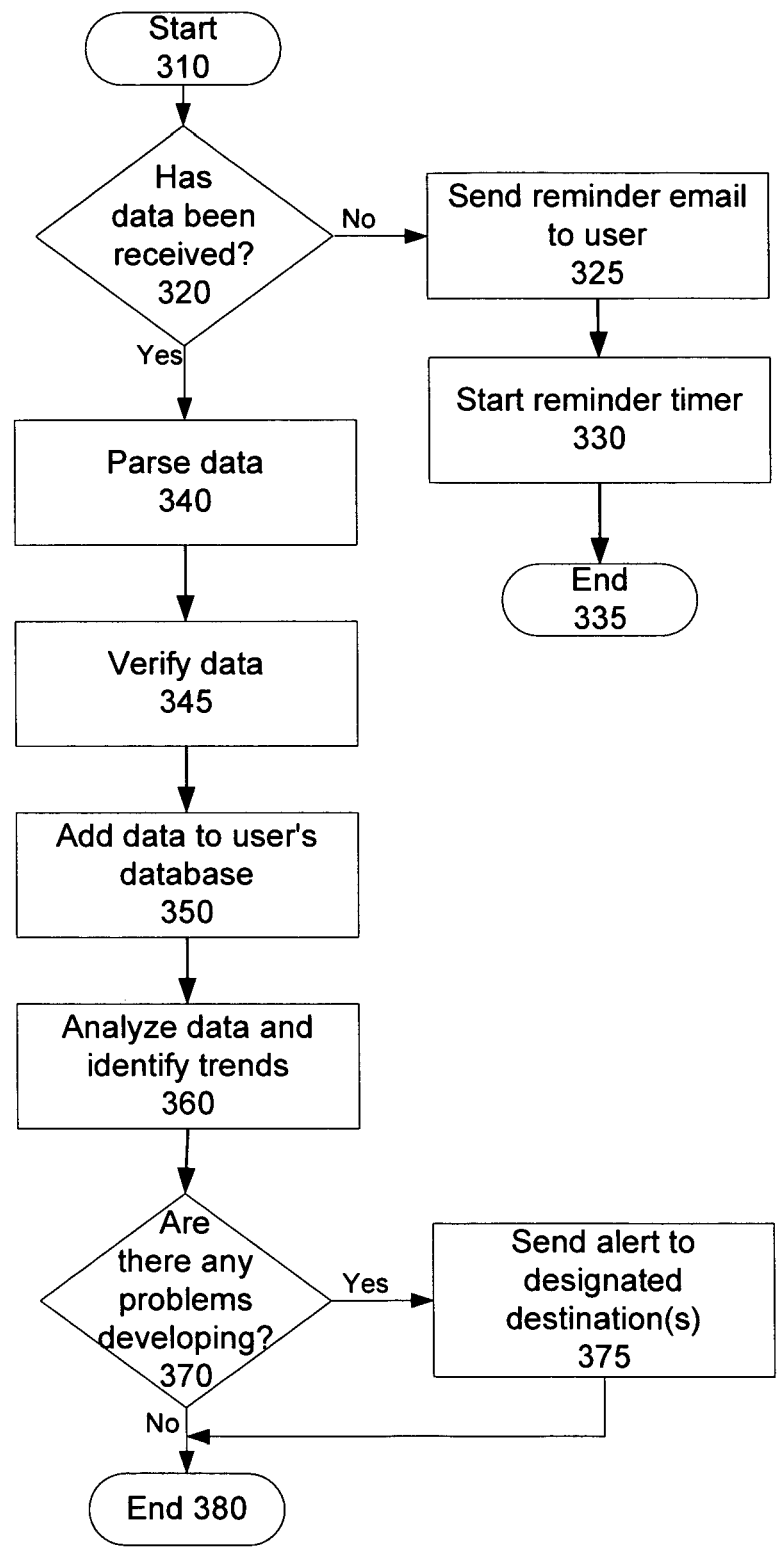
FIG. 3 is an overview flowchart of one embodiment of the process of obtaining data from an SMD, in accordance with the present invention.

FIG. 3 is an overview flowchart of one embodiment of the process of obtaining data from an SMD, in accordance with the present invention. The process starts at block 310. In one embodiment, a thread of this sort is spawned whenever a timer indicates that data should have been received from a user.

At block 320, the system determines whether data has been received. In one embodiment, data may be submitted via email. In another embodiment, data may be submitted via an instant messenger message. In another embodiment, data may be submitted via a web interface, a cellular telephone interface (SMS, MMS, etc.), or other means.

In one embodiment, speed dial SMS or email is used to report data. In one embodiment, the report may be done by holding down a button on a cellular telephone keypad. This triggers the display of an SMS or email template. The user fills in the values and then sends the data on to the system. If data has been received, the process continues to block 340. If no data has been received, the process continues to block 325.

In one embodiment, a web interface is used. FIG. 7 illustrates an exemplary web interface. The user logs into the web site. In one embodiment, this is a secure log-in. In one embodiment SSL or a similar security mechanism is used. In one embodiment, a single page is presented to the user which includes the ability to enter all measurements for a particular date. In one embodiment, the list of potential measurements for entry is limited to the measurements corresponding to the known devices of the user. In another embodiment, illustrated in FIG. 7, the user may select the test type data to enter 715. In one embodiment, the web page enables entry of data for one day at a time 705. In another embodiment, the user may select multiple dates on a single page. In one embodiment, the time associated with data is adjusted based on time zone 710. This ensures that the time associated with measurements is correct, regardless of the location of the user.

Returning to FIG. 3, At block 325, the process sends a reminder to the user. In one embodiment, the reminder is an email includes a pre-filled subject line, in which the user need only enter the basic data. For example, the reminder email may have the subject line: "BP ???/??? mmHg, HR ?? BPM, BG ??? mg/dL, time Dec. 12, 2005 8:00 am." The user can then enter the data for the question marks.

In one embodiment, a first reminder is sent automatically a short time before the data is expected from the user. In one embodiment, even if an automatic initial reminder is sent, an additional reminder is sent if the data is not received within the expected time frame.

At block 330, the process starts a reminder timer. The reminder timer spawns this process, when a preset time period has elapsed. In one embodiment, if no response is received to the reminder, the process is escalated. In one embodiment, there are secondary contacts, who are sent a reminder. In another embodiment, for certain situations, the user's care taker, supervisor, doctor, or other indicated person is notified.

In one embodiment, there may be an available escalation of reminders. For example, the first reminder is sent via email to the user only. A second reminder is sent via email and voicemail to the user. A third reminder is sent via email, voicemail, and/or fax to the user and another indicated person. In one embodiment, the user may indicate via email that he or she will not be entering data for a period of time (for example when the user goes on vacation in a location that does not have network availability.) In that case, in one embodiment, the timer is set such that the user is not reminded during the absent period. After the reminder is sent, the process ends, at block 335. As noted above, a new process is spawned when the timer, set at block 330, expires.

If, at block 325, data was received from the user, the process continued to block 340.

At block 340, the data is parsed. In one embodiment, the relevant data is included in the subject line. An exemplary subject line, for a blood pressure and heart rate monitor may appear as follows: "BP 120/95 mmHg, HR 75 BPM, BG 120 mg/dL, time Dec. 12, 2005 8:00 am." From an email containing this information, the system can parse the following data:

1. user identity (based on the sender data)
2. device used (based on corresponding monitors associated with the user
3. Blood pressure (BP 120/95)
4. Heart rate (75 BMP)
5. Blood Glucose level (120 mg/dL)
6. Date & time of measurement (Dec. 12, 2005 8:00 am)

This data is sufficiently complete that it can be used to completely populate an entry in the server.

In one embodiment, the process determines whether the data was sent via other means, i.e. other than email. In general, single data elements are sent via the subject line of an email. However, batch data may be sent by other means. For significantly larger data batch uploads, for example for a user who uploads their data once per week, or a doctor's office that deals with uploading data from many patients, various solutions may be used:

1. Multiple e-mails may upload the data piece by piece;
2. The data may be in the message body for more space;
3. An email template may be used, in which the user can fill in the data in a known format;
4. The data may be submitted via a web interface; or
5. Instant messenger, SMS, MMS, or other data entry methods may be used.

At block 345, the data is verified. The verification process is described in more detail below. Once verification is returned, the data is added to the server, at block 350. In one embodiment, the data is added immediately upon receipt, without the verification but is considered "temporary data" which can be rolled back. In one embodiment, this data is displayed to a user but is indicated as "unconfirmed." In one embodiment, the unconfirmed data may be indicated by a different color. In one embodiment, unconfirmed data is stored in a separate database from the permanent data. In one embodiment, unconfirmed data, if not confirmed, expires and is removed from the data set. In one embodiment, this may occur after a set number of reminders, a set period of time, after a set number of newer confirmed data points have been received, or after other criteria are met.

This data is then available to the user, and others who have access to the user's data. By making this data available, the system provides an always-on view of the user's current health state, even if the user's actual devices are not connected.

At block 360, trends are analyzed. Trends include changes over time in the readings provided by the user. For example, while minor changes in cholesterol level are not worrisome, a trend of increasing cholesterol levels over multiple weeks may be a signal of a problem developing. In one embodiment, the system analyzes trends using all of the available data to detect developing problems. Alternatively, various trends (for example cumulative trends analyzed over the last 30 days, 7 days, etc.) may be calculated and compared. In one embodiment, these trend calculations take into account data from multiple sources. For example, in addition to looking at blood pressure the analysis may also look at cholesterol levels. This may enable the system to derive a cumulative picture of the user's health, and changes in the user's health over time.

If there are any developing problems, an information alert is sent, at block 375. The alert is sent to the user, designated third parties, or any appropriate destinations which were designated when the user signed up.

The process ends at block 380.

Figure 4:
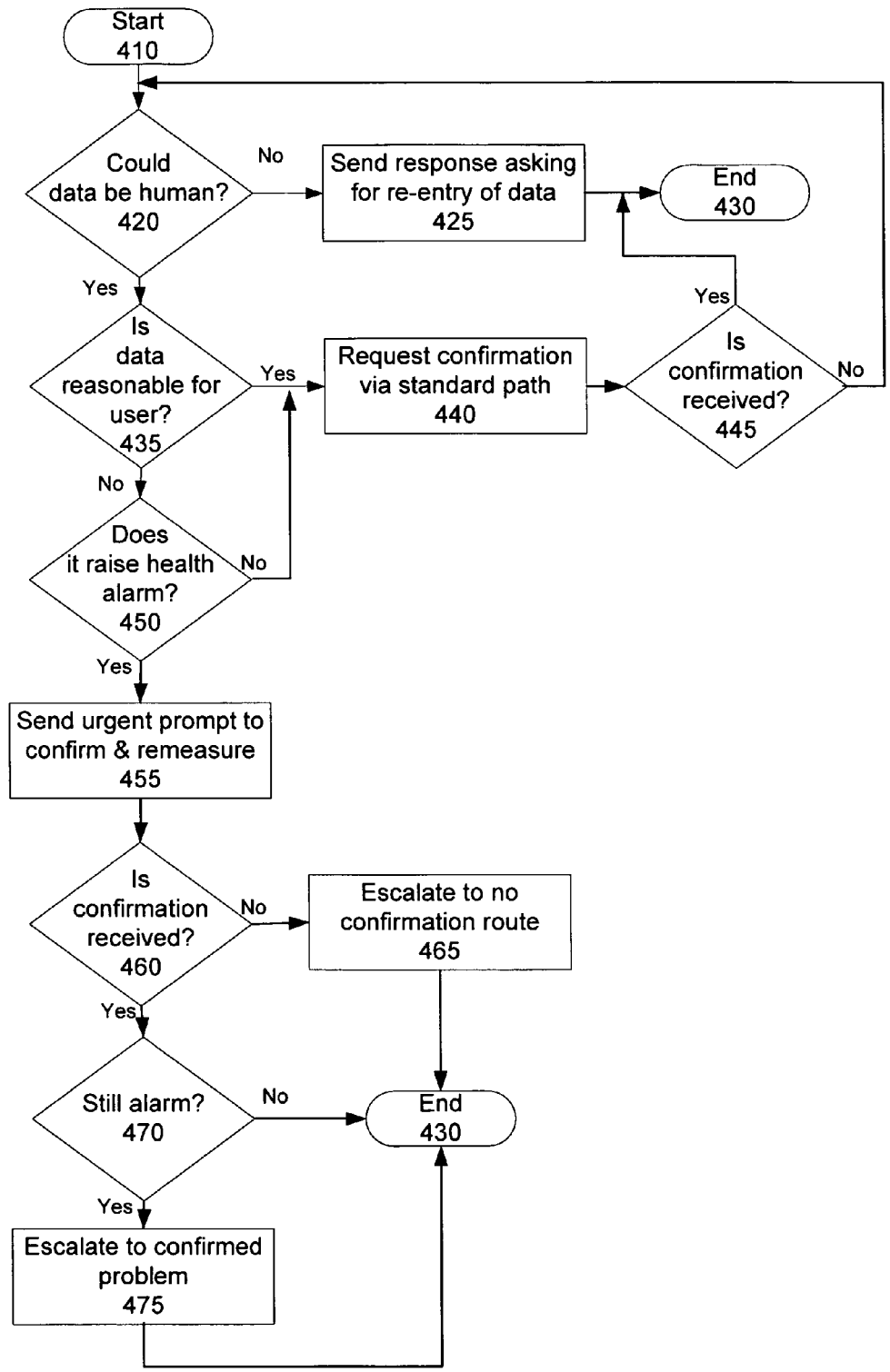
FIG. 4 is a flowchart of one embodiment of the data verification process.

FIG. 4 is a flowchart of one embodiment of the data verification process. Data flow is designed like a canal with multiple set of locks or holding tanks for data batches before it is added to the database. Accuracy checking is necessary because data is entered by users, who will occasionally make mistakes. In one embodiment, the system screens incoming data for accuracy and status changes in the user's health before adding it to the user's data pool. The process starts at block 410. In one embodiment, this process is invoked by the thread above, as indicated in block 345.

At block 420, the process determines whether the data could be accurate for a human being. For example a blood pressure that is 1000/9 is clearly not possible for a living human being. It is likely to be a typographic error. If the data is not possible for any human being, the process, at block 425, sends a response to the user asking for re-entry of the data. The process then terminates, at block 430. Note that in this instance the clearly wrong data is never added to the database. In the flowchart discussed above with respect to FIG. 3, the process terminates at block 345, since positive verification is never returned.

If the data is feasible, the process at block 435 determines whether the data is reasonable for the user in question. In one embodiment, this process uses the past history of the user's own data. The cumulative user data pool is used in evaluating the incoming user data.

If the data is reasonable (i.e. within normal parameters for the user), the process continues to block 440. Otherwise, the process continues to block 450.

The process requests a confirmation, via standard path, at block 440. In one embodiment, confirmation is sent as each data set is received. In another embodiment, data is collected and confirmations are only sent once a day or once per time period to validate the data. In one embodiment, the data is added to the user's data as "unconfirmed." In one embodiment, such unconfirmed data is flagged during display as unconfirmed. In one embodiment, such unconfirmed data is only moved to the permanent dataset when it is confirmed.

In one embodiment, the confirmation simply requests that the user reply affirmatively to the confirmation. In one embodiment, the confirmation e-mail is a serialized e-mail including a unique identifier. In one embodiment, this unique identifier is associated with the unconfirmed data. This enables a short email message (i.e. "correct" or selection of a radio button saying "yes this data is correct.") to be correctly associated with the data being confirmed. In one embodiment, the confirmation repeats the original data, and easily enables the user to correct any errors. Again, depending on the size of the data batch to be validated, the system may use the message body as well as the subject line.

At block 445, the process determines whether confirmation has been received. If the user's response makes a correction, i.e. it is not a confirmation, the process returns to block 420, to reverify the data. If the confirmation OKs the data, the data is tagged as validated, and the process ends at block 430. In one embodiment, if no confirmation is received, a reminder is sent. In one embodiment, the reminders are escalated, if no confirmation is received. Escalation may include contacting the user through other channels, contacting secondary/supervisory users, etc.

If, at block 435, the data was deemed to be unreasonable, the process continued to block 450. At block 450, the process determines whether the problem is something that should raise a health alarm. If no alarms are raised, the process continues to block 440, to request confirmation via a standard path. If any alarms are raised, the process continues to block 455.

If an alarm is raised, at block 455, in one embodiment, the user is urgently prompted to confirm that data point was indeed correctly entered. In one embodiment, the user is asked to perform a secondary test to confirm the results. The process then determines whether a confirmation is received, at block 460. In one embodiment, if no response is received to the confirmation request, the response level is escalated, at block 465. If a confirmation is received, the process continues to block 470.

At block 470, the process determines whether there is still an alert, based on the confirmation and secondary measurements. If the alarm is no longer in place, it means that the user corrected the data/measurements and now the monitored variables are within the expected parameters. In that case, the data is tagged as validated, and the process ends at block 430.

If the alarm persists, then at block 475, the relevant parties for the alert are identified, based on the specific alarm and severity. This will vary for the parameter being measured. If it is a life threatening or otherwise critical parameter, the user and healthcare providers will be contacted immediately to determine if there is actual danger. In one embodiment, for sufficiently severe (and in one embodiment confirmed) health alarms, 911 may be contacted. In most cases, however, the user is unlikely to be entering data when having a heart attack or similarly severe event.

Figure 5:
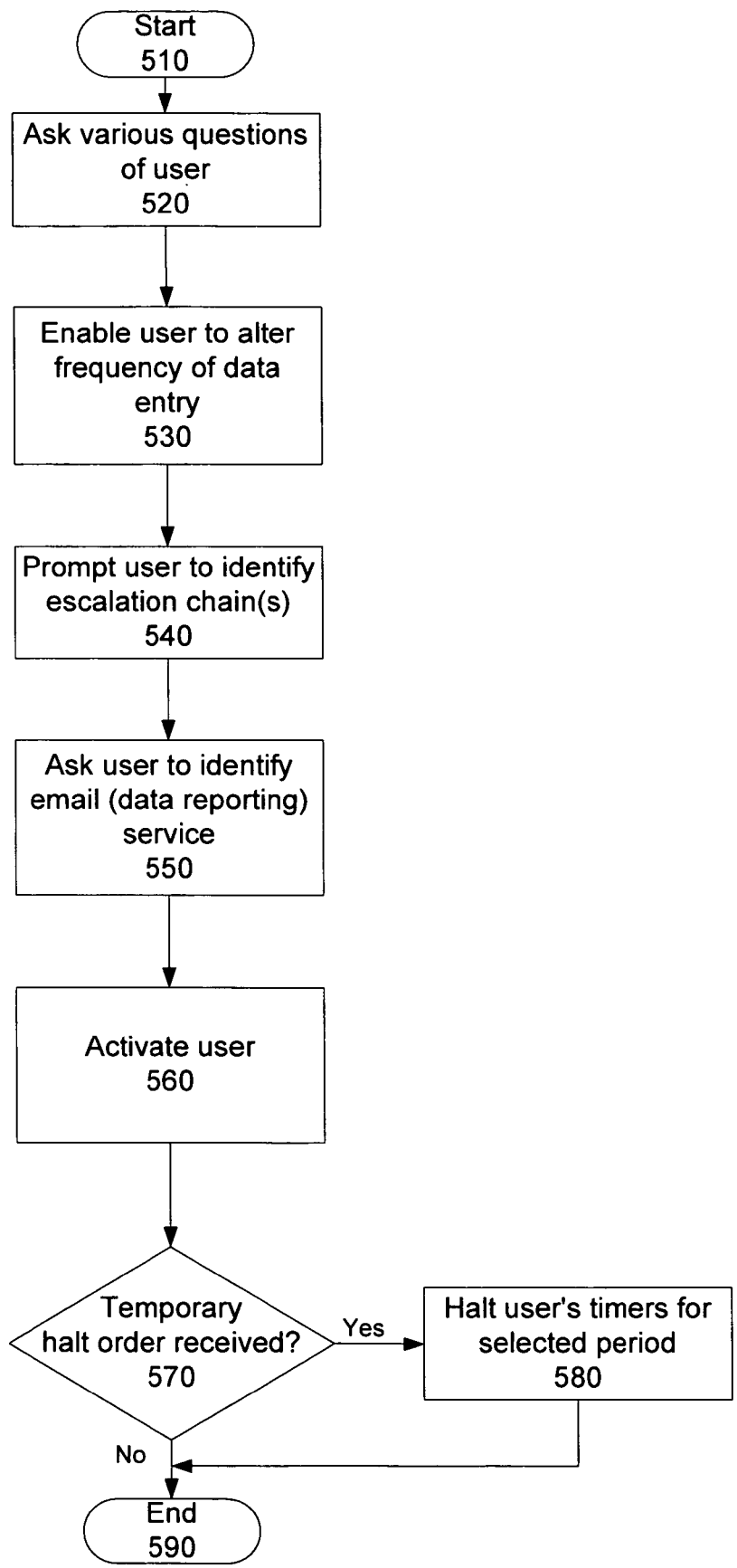
FIG. 5 is a flowchart of one embodiment of configuring the system.

FIG. 5 is a flowchart of one embodiment of configuring the system. The process starts at block 510, when a user subscribes to this feature. In one embodiment, this process may be done at the health clinic or doctor's office for medical SMDs. In that case, in one embodiment, the "user" for this figure may be an administrator, rather than the user who will enter data.

At block 520, various questions are asked of the user. In one embodiment, the system may include a health questionnaire. In one embodiment, the user is requested to identify all SMDs associated with the user.

At block 530, the frequency of data entry is selected. In one embodiment, the user is strongly encouraged to send the data as frequently as the SMDs provide it. In one embodiment, a user can set preferences for submitting data via email, IM, web interface, etc.

Figure 6:
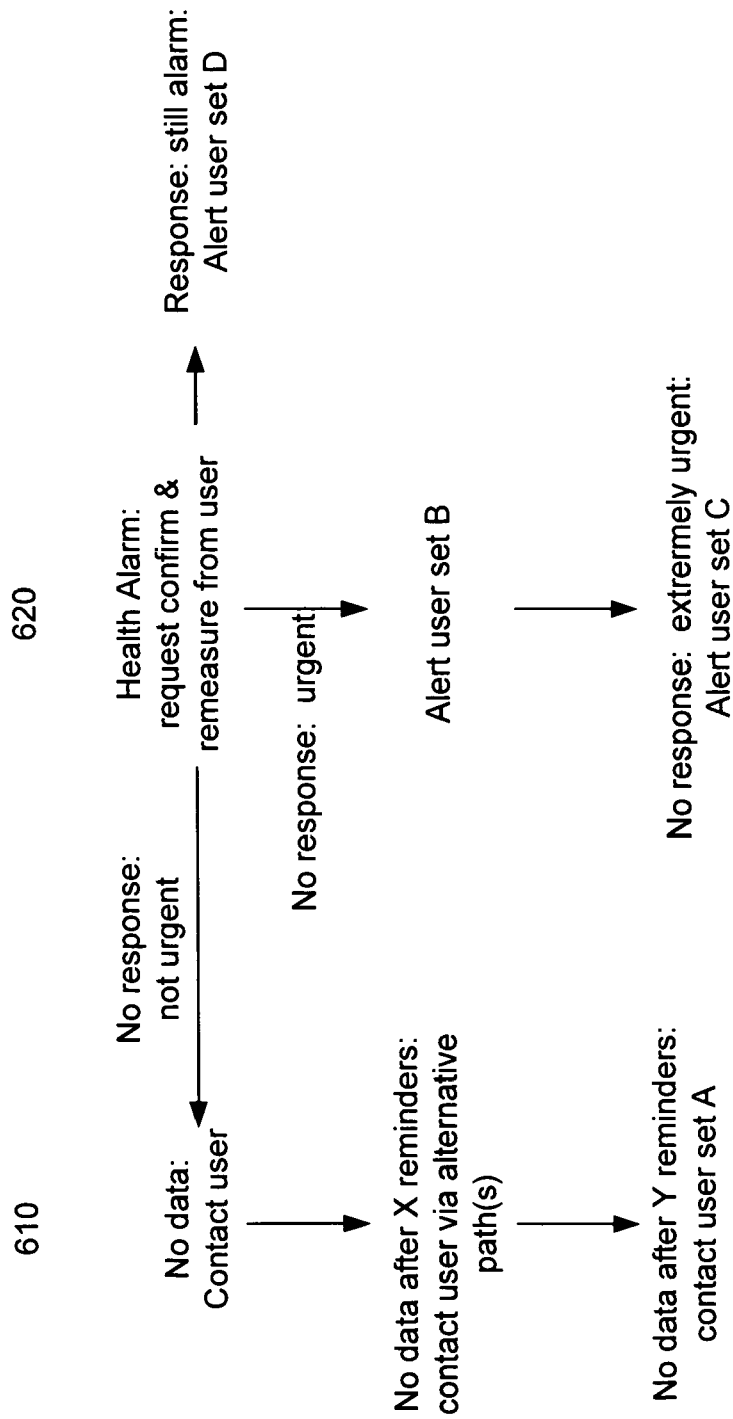
FIG. 6 illustrates an exemplary escalation chain.

At block 540, the user's escalation chain is identified. The user may indicate how contacts should proceed, in case there is a health alarm. An exemplary escalation chain is shown in FIG. 6.

The reminder escalation 610 may be as follows: if no data is received when it is expected, the user is contacted via ordinary means. If no data is received after a set number of reminders (for example two consecutive reminders), the user is contacted via an alternative method. If no data is received after a set number of alternative contacts, a secondary user is alerted.

The health alarm escalation 620 may be as follows: if there is a health alarm based on received data, the user is contacted and requested to confirm the information & retake the test to verify the results. If no response is received, and the health alarm is not urgent, the reminder escalation 610 is used. If the health alarm is urgent, a secondary user (who may be different from the secondary user in the reminder escalation 610) is alerted. If the health alarm is truly urgent (i.e. potentially life threatening) a different designated user may be alerted. In one embodiment, the different designated user may be 911, a doctor, or any other entity or entities. Note that this is just an exemplary escalation path. For example, for a child user, the escalation may directly go to alerting a parent or guardian even at the first failure to enter data. Alternative escalation paths would be understood.

Returning to FIG. 5, at block 550, in one embodiment, the user is asked to specify which e-mail, or other data reporting, service they use (i.e. web mail, OUTLOOK™ email, SMS, mobile devices such as BLACKBERRY™ device, etc.) The system uses this information to optimize the format of the reminder e-mails and other templates for the user's e-mail service.

In one embodiment, these forms are pre-populated, and the user is simply provided a chance to make any changes.

At block 560, the user is activated. In one embodiment, this includes starting various timers which send alerts and prompt the user.

At block 570, the process determines whether a temporary halt order has been received from the user. If so, at block 580 the user's timers are halted, for the period of time specified by the halt order. This would ensure that a user on vacation, or otherwise out of contact, would not result in ever more dire reminders. The process ends at block 590.

Figure 8:
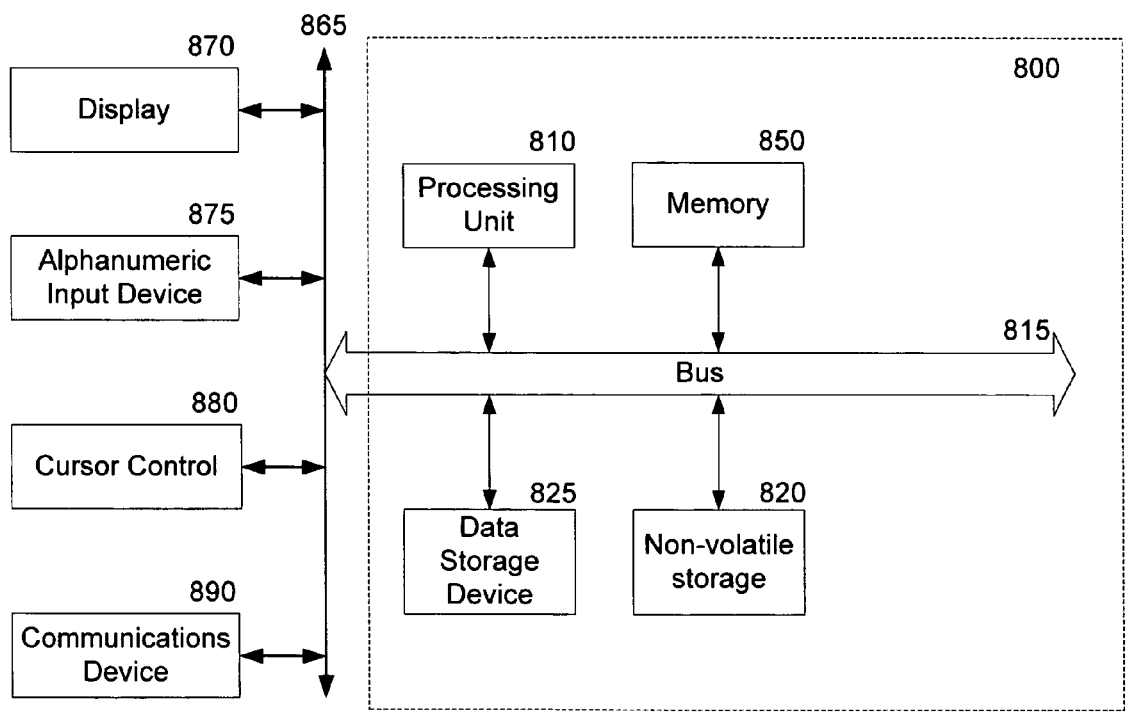
FIG. 8 is one embodiment of a computer system in accordance with the present invention.

FIG. 8 is one embodiment of a computer system that may be used with the present invention. It will be apparent to those of ordinary skill in the art, however that other alternative systems of various system architectures may also be used.

The data processing system illustrated in FIG. 8 includes a bus or other internal communication means 815 for communicating information, and a processor 810 coupled to the bus 815 for processing information. The system further comprises a random access memory (RAM) or other volatile storage device 850 (referred to as memory), coupled to bus 815 for storing information and instructions to be executed by processor 810. Main memory 850 also may be used for storing temporary variables or other intermediate information during execution of instructions by processor 810. The system also comprises a read only memory (ROM) and/or static storage device 820 coupled to bus 815 for storing static information and instructions for processor 810, and a data storage device 825 such as a magnetic disk or optical disk and its corresponding disk drive. Data storage device 825 is coupled to bus 815 for storing information and instructions.

The system may further be coupled to a display device 870, such as a cathode ray tube (CRT) or a liquid crystal display (LCD) coupled to bus 815 through bus 865 for displaying information to a computer user. An alphanumeric input device 875, including alphanumeric and other keys, may also be coupled to bus 815 through bus 865 for communicating information and command selections to processor 810. An additional user input device is cursor control device 880, such as a mouse, a trackball, stylus, or cursor direction keys coupled to bus 815 through bus 865 for communicating direction information and command selections to processor 810, and for controlling cursor movement on display device 870.

Another device, which may optionally be coupled to computer system 800, is a communication device 890 for accessing other nodes of a distributed system via a network. The communication device 890 may include any of a number of commercially available networking peripheral devices such as those used for coupling to an Ethernet, token ring, Internet, or wide area network. The communication device 890 may further be a null-modem connection, or any other mechanism that provides connectivity between the computer system 800 and the outside world. Note that any or all of the components of this system illustrated in FIG. 8 and associated hardware may be used in various embodiments of the present invention.

It will be appreciated by those of ordinary skill in the art that any configuration of the system may be used for various purposes according to the particular implementation. The control logic or software implementing the present invention can be stored in main memory 850, mass storage device 825, or other storage medium locally or remotely accessible to processor 810.

It will be apparent to those of ordinary skill in the art that the system, method, and process described herein can be implemented as software stored in main memory 850 or read only memory 820 and executed by processor 810. This control logic or software may also be resident on an article of manufacture comprising a computer readable medium having computer readable program code embodied therein and being readable by the mass storage device 825 and for causing the processor 810 to operate in accordance with the methods and teachings herein.

The present invention may also be embodied in a handheld or portable device containing a subset of the computer hardware components described above. For example, the handheld device may be configured to contain only the bus 815, the processor 810, and memory 850 and/or 825. The handheld device may also be configured to include a set of buttons or input signaling components with which a user may select from a set of available options. The handheld device may also be configured to include an output apparatus such as a liquid crystal display (LCD) or display element matrix for displaying information to a user of the handheld device. Conventional methods may be used to implement such a handheld device. The implementation of the present invention for such a device would be apparent to one of ordinary skill in the art given the disclosure of the present invention as provided herein.

The present invention may also be embodied in a special purpose appliance including a subset of the computer hardware components described above. For example, the appliance may include a processor 810, a data storage device 825, a bus 815, and memory 850, and only rudimentary communications mechanisms, such as a small touch-screen that permits the user to communicate in a basic manner with the device. In general, the more special-purpose the device is, the fewer of the elements need be present for the device to function. In some devices, communications with the user may be through a touch-based screen, or similar mechanism.

It will be appreciated by those of ordinary skill in the art that any configuration of the system may be used for various purposes according to the particular implementation. The control logic or software implementing the present invention can be stored on any machine-readable medium locally or remotely accessible to processor 810. A machine-readable medium includes any mechanism for storing or transmitting information in a form readable by a machine (e.g. a computer). For example, a machine readable medium includes read-only memory (ROM), random access memory (RAM), magnetic disk storage media, optical storage media, flash memory devices, etc.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. An apparatus to provide user data through an always-on virtual monitor, alert, control, and share (MACS) device on a computer system comprising:
   a processor to execute instructions for the always-on virtual MACS device, wherein the instructions cause the processor to include:
      a data receiving logic to receive intermittent data from a user about readings from a real sensor, monitor or device (SMD), and to add the data to a database without verifying the data;
      a verification engine to perform a two phase verification of the data to verify that the data is accurate, wherein a first phase of the two phase verification includes determining whether the data could be accurate for a human being and a second phase of the two phase verification includes determining whether the data is reasonable for the user, wherein the second phase is not performed if the data could not be accurate for a human being, wherein unverified data expires and is removed from the database if verification of the unverified data is not performed within a specified time period;
      an intelligent notification engine to communicate with the user; and
      a presentation layer to enable a user to interface with the always-on virtual MACS device, the always-on virtual MACS device representing the real SMD, and providing data regardless of a status of the real SMD.

2. The apparatus of claim 1, wherein the data receiving logic is designed to receive data entered via e-mail.

3. The apparatus of claim 2, wherein the data entered via e-mail is formatted in a subject line of the email.

4. The apparatus of claim 1, further comprising the instructions to cause the processor to include:
   a reminder logic to send a reminder message to the user to enter the data.

5. The apparatus of claim 4, wherein the reminder message comprises a template form that is filled in by the user.

6. The apparatus of claim 4, further comprising the instructions to cause the processor to include:
   an escalation logic to escalate the process if no response is received to the reminder message.

7. The apparatus of claim 6, further comprising the instruction to cause the processor to include:
   a snooze logic to, upon receiving a snooze signal, prevent the escalation logic from escalating the process for a period of time.

8. The apparatus of claim 4, further comprising the instructions to cause the processor to include:
   a configuration logic to enable a user to place a temporary hold, the temporarily hold disabling the reminders message.

9. The apparatus of claim 1, further comprising:
   the verification logic to determine if the data triggers an alert, based on the user's past data.

10. The apparatus of claim 9, further comprising:
    the intelligent notification logic to notify a predesignated party if the data triggers the alert.

11. The apparatus of claim 9, further comprising:
    the verification logic requesting a verification of the data by the user, and a re-measurement by the user, if the data triggers an alert.

12. The apparatus of claim 1, further comprising the instructions to cause the processor to include:
   a data mining engine to analyze cumulative user data collected from a plurality of sensors and identify data trends.

13. The apparatus of claim 12, wherein the data mining engine may trigger an alert, if the data trends are indicating a problem.

14. The apparatus of claim 1, wherein the database is a historical database where verified data is already stored.

15. A non-transitory machine-readable medium having stored thereon data representing sets of instructions which, when executed by a machine, cause the machine to:
   receive intermittent data from a user about readings from a real sensor, monitor or device (SMD);
   add the data to a database without verifying the data;
   perform a two phase verification of the data to verify that the data is accurate, wherein a first phase of the two phase verification includes determining whether the data could be accurate for a human being and a second phase of the two phase verification includes determining whether the data is reasonable for the user, wherein the second phase is not performed if the data could not be accurate for a human being;
   remove unverified data from the database if verification of the unverified data is not performed within a specified time period;
   communicate with the user; and
   provide an interface with an always-on virtual monitor, alert, control, and share (MACS) device, the always-on virtual MACS device representing the real SMD, and providing data regardless of a status of the real SMD.

16. The machine readable medium of claim 15, wherein the instructions further cause the machine to receive data entered via e-mail.

17. The machine readable medium of claim 16, further comprising:
   sending a reminder message to the user to enter data, the reminder message comprising a template form that is filled in by the user.

18. The machine readable medium of claim 15, further comprising:
   determining when the data triggers an alert, based on the user's past data.

19. The machine readable medium of claim 18, further comprising:
   requesting a verification of the data by the user, and a re-measurement by the user, if the data triggers an alert.

20. The machine readable medium of claim 15, further comprising:
   analyzing cumulative user data and identify data trends.

* * * * *